United States Patent
Chao et al.

(10) Patent No.: US 9,980,967 B1
(45) Date of Patent: *May 29, 2018

(54) METHOD FOR OVERCOMING DRUG RESISTANCE OF EGFR MUTATION AND CANCEROUS STEMNESS OF HUMAN NON-SMALL CELL LUNG CARCINOMA

(71) Applicant: NATIONAL CHIAO TUNG UNIVERSITY, Hsinchu (TW)

(72) Inventors: Jui-I Chao, Hsinchu County (TW); Kuang-Kai Liu, Taoyuan (TW); Ya-Ping Hsu, Taichung (TW)

(73) Assignee: National Chiao Tung University, Hsinchu (TW)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/460,500

(22) Filed: Mar. 16, 2017

(51) Int. Cl.
*C07D 239/94* (2006.01)
*A61K 31/517* (2006.01)

(52) U.S. Cl.
CPC .................. *A61K 31/517* (2013.01)

(58) Field of Classification Search
CPC ..................... A61K 31/517; C07D 239/94
See application file for complete search history.

(56) References Cited

U.S. PATENT DOCUMENTS

| | | | |
|---|---|---|---|
| 5,770,599 | A | 6/1998 | Gibson |
| 8,501,413 | B2 | 8/2013 | Varmus et al. |
| 8,546,107 | B2 | 10/2013 | Freeman et al. |
| 9,512,086 | B2 | 12/2016 | Chao et al. |
| 2005/0272083 | A1 | 12/2005 | Seshagiri |
| 2016/0068495 | A1 | 3/2016 | Chao et al. |

FOREIGN PATENT DOCUMENTS

| | | |
|---|---|---|
| CN | 105503746 A | 4/2016 |
| TW | 201609672 A | 3/2016 |

OTHER PUBLICATIONS

Yin et al. Bioorganic & Medicinal Chemistry Letters, 2014, vol. 24, pp. 5247-5250.*
Jui-I Chao, Ya-Ping Hsu, Kuang-Kai Liu, Chien-Jen Chang, Chinpiao Chen; SP101, A Novel Synthetic Compound Reduces the Drug Resistance of EGFR (T790M) and Cancerous Sternness in Non-Small Cell Lung Carcinoma; Experimental Biology 2016, San Diego Convention Center, Sails Pavilion, National Chiao Tung University, Taiwan, R.O.C.; Apr. 6, 2016.

* cited by examiner

*Primary Examiner* — Samira Jean-Louis
(74) *Attorney, Agent, or Firm* — Rosenberg, Klein & Lee

(57) ABSTRACT

EGFR mutation (T790M) and cancerous stemness have shown drug resistances in human non-small-cell lung cancer (NSCLC), thus development of novel drugs in overcoming drug resistances in the NSCLC therapy is highly desired. SP101 is a novel gefitinib derivative, which can bind the ATP-binding pocket of EGFR to inhibit its EGFR kinase activity. SP101 can reduce the drug resistances of EGFR mutation (T790M) and cancerous stemness in NSCLC. SP101 induced cancer cell death and apoptosis in the gefitinib-resistant EGFR mutation (T790M) H1975 cells. SP101 inhibited phosphorylated EGFR and its downstream Survivin proteins but conversely induced Caspase 3 activation for apoptosis induction. Moreover, SP101 could decrease Oct4 protein level and reduce Survivin proteins but conversely elicited active Caspase 3 in the xenograft human H1975 lung tumors in nude mice.

8 Claims, 22 Drawing Sheets
(9 of 22 Drawing Sheet(s) Filed in Color)

METHOD FOR OVERCOMING DRUG RESISTANCE OF EGFR MUTATION AND CANCEROUS STEMNESS OF HUMAN NON-SMALL CELL LUNG CARCINOMA

BACKGROUND OF THE INVENTION

1. Field of the Invention

This invention relates to utilize a new compound to treat human non-small cell lung carcinoma, more particularly, to utilize the compound for overcoming drug resistance of EGFR mutation and cancerous stemness in the above mentioned disease.

2. Description of Related Art

There are two main types of lung cancer; one is small cell lung carcinoma (SCLC) (15%~25% of cases), the other is non-small cell lung carcinoma (NSCLC) (75%~80% of cases). The epidermal growth factor receptor (EGFR) is a tyrosine kinase receptor which belongs to the ErbB family, EGFR overexpresses in many types of cancers, including 25% of lung cancer and occurs in 40%~80% of patients with NSCLC which is a promising therapeutic target.

Abnormal activation of tyrosin kinase increases cell proliferation, survival, and cytotoxic drug resistance of malignant cells. Approximately 90% of EGFR mutations are exon 19 deletions and exon 21 L858R point mutations which are associated with sensitivity to the small-molecule kinase inhibitors in treating cancer. L858R point mutation of EGFR seemed to cause the repositioning of crucial residues that surround the ATP-binding cleft of the EGFR tyrosine kinase domain to result in small molecule tyrosine kinase inhibitors (TKIs) such as Gefitinib inhibiting EGFR mutation by competing with ATP binding within the catalytic kinase domain of tyrosine kinase receptor.

Although EGFR TKI has revolutionized treatment of EGFR-mutant NSCLC, most patients acquired resistance after several months' treatment. EGFR mutation such as T790M mutation correlates resistance to EGFR TKI treatment which can be detected approximately 50%~60% after resistance develops. T790M the most common secondary point mutation in which methionine is to substitute threonine at amino acid position 790 is one of the mutations identified from the NSCLC patients acquiring resistance to Gefitinib. T790M mutation increases the affinity of the receptor for ATP, thereby reducing the effectiveness of TKI, Gefitinib.

SUMMARY OF THE INVENTION

Development of novel drugs for overcoming drug resistance in NSCLC therapy is highly desired. This invention provides a Gefitinib derivative, Dodecyl-4-(4-(3-(4-(3-chloro-4-fluorophenylamino)-7-methoxyquinazolin-6-yloxy)propyl)piperazin-1-yl)-4-oxobutanoate, hereinafter referred to as SP101. The chemical structure of SP101 is as follows:

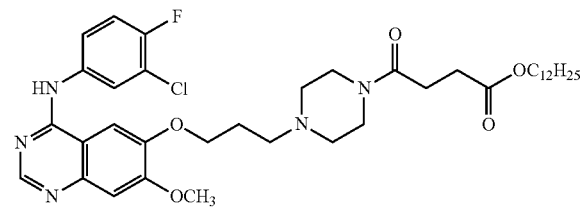

SP101 can bind the ATP-binding pocket of EGFR to inhibit its EGFR kinase activity. The EGFR mutation at T790M and cancerous stemness are associated with drug resistance in NSCLC therapy. In this invention, SP101 shows the ability to reduce drug resistances of EGFR (T790M) and cancerous stemness in NSCLC. SP101 displays the anticancer ability in inducing cell death and apoptosis in the Gefitinib-resistant EGFR (T790M) of H1975 cells. SP101 inhibits the phosphorylated EGFR and its downstream surviving protein expression and induced the caspase 3 activation for apoptosis induction.

Moreover, SP101 is more potent on the reduction of cell viability than Gefitinib and also induced more apoptosis than Gefitinib in the A549-ON which expressed Oct4 and Nanog proteins in lung cancer cells displaying cancerous stemness and drug resistance. In addition, SP101 is more effective in inducing cell death and apoptosis than Gefitinib in the PLC26 cells which were from clinical lung cancer patients having Gefitinib-drug resistance. More importantly, SP101 significantly inhibits drug-resistant tumor growth in the xenograft human lung tumors in nude mice.

BRIEF DESCRIPTION OF THE DRAWING

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENTS

Figure 1:
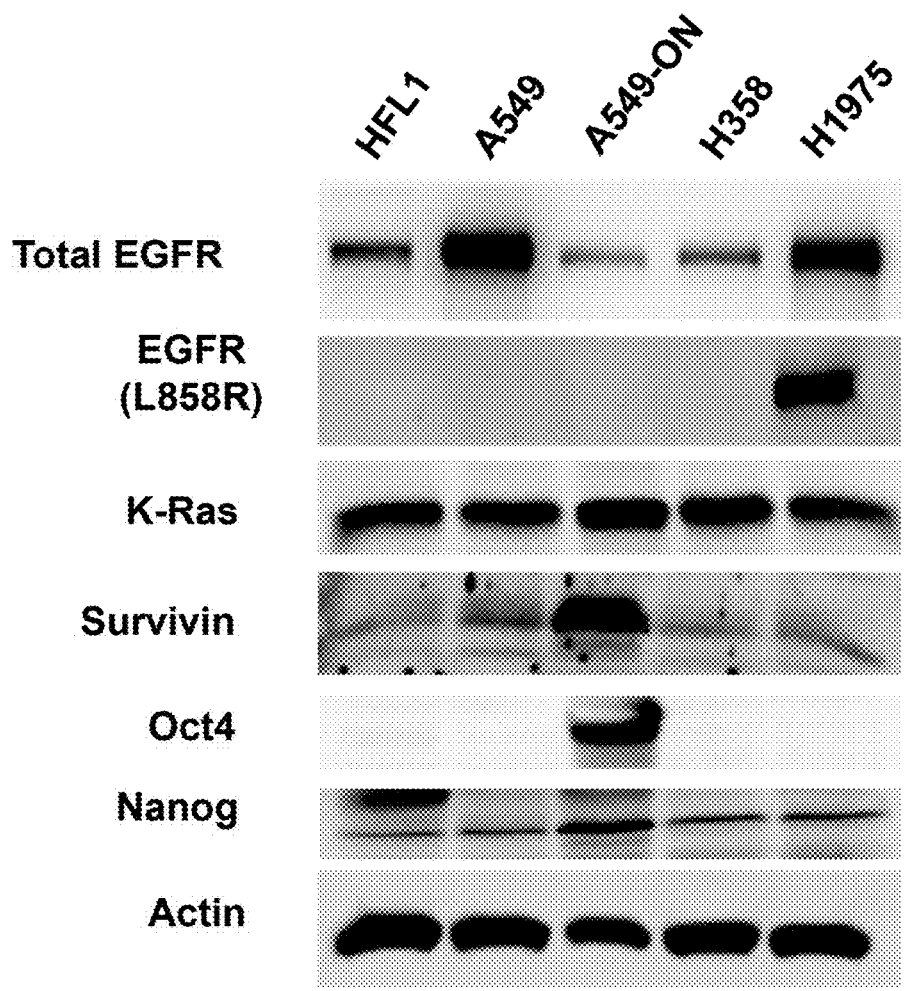
FIG. 1 shows the protein levels of EGFR, K-Ras Survivin and stem cell markers (Oct4 and Nanog) in normal lung fibroblast and various NSCLC cell lines.

A detailed description of this invention is illustrated by the following specific embodiments. Person skilled in the art can conceive other advantages and effects of this invention based on the disclosure contained in the specification of this invention. This invention can be executed or applied by the other methods. Without affecting the purpose of this invention, any detail in the description can be modified or changed based on different viewpoints and applications and it shall still be covered within the scope of this invention.

I. Preparation of SP101

The detailed synthesis process of SP101 is disclosed in U.S. Pat. No. 9,512,086 filed on Jan. 14, 2015, the entire content of which is incorporated herein by reference.

(1). Synthesis of Compound-1:
4-methoxy-4-oxobutanoic acid (Step 1)

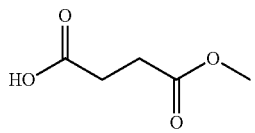

A mixture of succinic anhydride (1.00 g, 10.00 mmol) and dry methanol (20 mL 500 mmol) was stirred vigorously while heated at reflux 2.5 hours. The excess of methanol was removed under reduced pressure and the residue was taken up in water, and the solution was extracted with dichloromethane (hereinafter referred to DCM), dried over $MgSO_4$, and evaporated to obtain Compound-1 (0.90 g, 6.81 mmol) in 68% yield.

$^1$H NMR (400 MHz, $CDCl_3$, δ): 10.89 (b, 1H), 3.70 (s, 3H), 2.71-2.61 (m, 4H); $^{13}$C NMR (100.6 MHz, $CDCl_3$, δ): 178.1, 172.6, 51.9, 28.8, 28.6; IR (KBr): 3028, 2957, 1736, 1690, 1175, 1003 cm$^{-1}$; MS m/z: 132.0 (M$^+$, 0.1), 114.1 (11.2), 101.0 (100.0), 73.1 (20.9), 59.1 (17.2), 55.0 (41.8); HRMS-EI (m/z): [M]$^+$ calculated for $C_5H_8O_4$, 132.0423; found, 132.0424.

(2). Synthesis of Compound-2: methyl 4-(4-benzylpiperazin-1-yl)-4-oxobutanoate (Step 2)

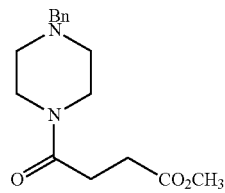 [SMILES: COC(=O)CCC(=O)N1CCN(Cc2ccccc2)CC1]

A solution of Compound-1 (0.35 g. 2.65 mmol) and thionyl chloride (0.22 mL, 2.9 mmol) in benzene (5 mL) was refluxed for 1.5 hours. Subsequently, the majority of the thionyl chloride and benzene were removed by distillation. The mixture was cooled down to room temperature and dried under a vacuum to give a crude 3-chlorocarbonylpropionic acid methyl ester. A solution of 3-chlorocarbonylpropionic acid methyl ester (0.5 g, 2 mmol) in dichloromethane (5 mL) was added to a round flask containing 1-benzylpiperazin (0.50 g, 2.84 mmol) in dichloromethane through cannula, and subsequently pyridine (0.65 mL, 8.00 mmol) was added. The resulting solution was stirred at room temperature overnight, and quenched by adding water. The pH of the solution was made basic (pH 9), by adding 2 M NaOH solution. The solution was extracted with dichloromethane, dried over $MgSO_4$, and evaporated to give a crude residue which was purified by column chromatography, eluting by ethyl acetate/hexane (1:2.3, 1:1, 3:1) to provide Compound-2 (0.26 g, 0.90 mmol) in 34% yield.

$^1$H NMR (400 MHz, $CDCl_3$, δ): 7.32-7.29 (m, 4H), 7.28-7.27 (m, 1H), 3.69 (s, 3H), 3.63-3.60 (t, J=5.1 Hz, 2H), 3.51 (s, 2H), 3.49-3.47 (t, J=5.1 Hz, 2H), 2.68-2.59 (m, 4H), 2.45-2.39 (m, 4H); $^{13}$C NMR (100.6 MHz, $CDCl_3$, δ): 173.7, 169.5, 137.6, 129.1, 128.3, 127.3, 62.9, 52.9, 52.7, 51.8, 45.3, 41.8, 29.1, 27.9; IR (KBr): 2949, 1736, 1646, 1438, 1226, 1165, 998, 744 cm$^{-1}$; MS in/z: 290.1 (M$^+$, 14.0), 259.1 (16.4), 146.1 (48.7), 134.1 (21.5), 91.1 (100.0); HRMS-EI (m/z): [M]$^+$ calculated for $C_{16}H_{22}N_2O_3$, 290.1630; found, 290.1634.

(3). Synthesis of Compound-3: methyl 4-(4-(3-chloropropyl)piperazin-1-yl)-4-oxobutanoate (Step 3)

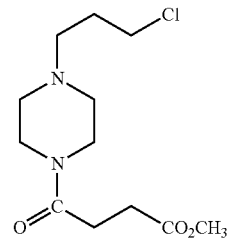 [SMILES: COC(=O)CCC(=O)N1CCN(CCCCl)CC1]

A mixture of Compound 2 (0.21 g, 0.72 mmol) and 10% palladium on carbon (Pd/C) (22 mg. 10 wt %) in methanol (20 mL) in a Parr glass vessel and carefully flushed three times with hydrogen gas. The vessel was finally charged with hydrogen gas (60 psi) and shaken mechanically for 12 hours. After completion of the reaction, the reaction mixture was filtered through a pad of celite and washed with, excess methanol. The filtrate was concentrated under reduced pressure to obtain 4-oxo-4-piperazin-1-yl-butyric acid methyl ester (0.095 g, 0.48 mmol) in 66% yield. 4-oxo-4-piperazin-1-yl-butyric acid methyl ester was dissolved in tetrahydrofuran (hereinafter referred to THF) (10 mL), and subsequently added triethylamine (0.08 mL, 0.57 mmol) and 1-bromo-3-chloropropane (0.057 mL, 0.57 mmol). The solution was stirred at room temperature overnight. The reaction mixture was quenched by adding water. The resulting solution was extracted with ethyl acetate, dried over $MgSO_4$, and evaporated to give a residue purified by column chromatography ($Al_2O_3$), eluting by ethyl acetate to provide Compound-3 (0.024 g, 0.087 mmol) in 18% yield.

$^1$H NMR (400 MHz, $CDCl_3$, δ): 3.67 (s, 3H), 3.60-3.57 (t, J=6.3 Hz, 4H), 3.48-3.45 (t, J=5.1 Hz, 2H), 2.66-2.58 (m, 4H), 2.49-2.46 (t, J=7.1 Hz, 2H), 2.43-2.41 (t, J=5.0 Hz, 2H), 2.39-2.36 (t. J=5.1 Hz, 2H), 1.95-1.88 (m, 2H); $^1$C NMR (100.6 MHz, $CDCl_3$, δ): 173.6, 169.5, 55.1, 53.3, 52.8, 51.8, 45.2, 43.0, 41.7, 29.7, 29.0, 27.9; IR (KBr): 2950, 2814, 1736, 1647, 1438, 1369, 1227, 1168 cm$^{-1}$; MS m/z: 276.1 (M$^+$, 8.6), 245.1 (28.2), 213.1 (100.0), 132.1 (15.4); HRMS-EI (m/z): [M]$^+$ calculated for $C_{12}H_{21}ClN_2O_3$, 276.1241; found, 276.1242.

(4). Synthesis of Compound-4: 4-(3-chloro-4-fluorophenylamino)-7-methoxyquinazolin-6-ol (Step 4)

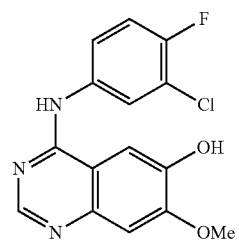 [SMILES: COc1cc2ncnc(Nc3ccc(F)c(Cl)c3)c2cc1O]

A mixture of 6-(benzyloxy)-N-(3-chloro-4-fluorophenyl)-7-methoxyquinazolin-4-amine (0.15 g, 0.37 mmol) and 10% Pd/C (25 mg, 10 wt %) in methanol (20 mL) in a Pan glass vessel and carefully flushed three times with hydrogen gas. The vessel was finally charged with hydrogen gas (60 psi) and shaken mechanically for 24 hours. After completion of the reaction, the reaction mixture was filtered through a pad of celite and washed with excess methanol. The filtrate was concentrated under reduced pressure to obtain Compound-4 (96 mg, 0.3 mmol) in 82% yield.

(5). Synthesis of Compound-5:
1-(3-chloropropyl)-piperazine hydrocloride (Step 5)

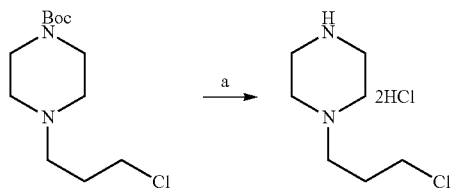 [SMILES: CC(C)(C)OC(=O)N1CCN(CCCCl)CC1 ; ClCCCN1CCNCC1]

1-(3-chloropropyl)-4-(t-butyloxycarbonyl)-piperaxine (4.0 g, 15.2 mmol) was treated with hydrochloric acid in ethyl acetate to obtain Compound-5 (3.17 g, 13.5 mmol) in yield 89%.

$^1$H NMR (400 MHz, D$_2$O, δ): 3.63-3.54 (m, 9H), 3.39 (s, 1H), 3.40-3.35 (m, 2H), 2.21-2.14 (m, 2H). $^{13}$C NMR (100.6 MHz, D$_2$O, δ): 54.8, 48.6, 41.1, 40.7, 26.2. IR (KBr): 3356, 3001, 1443, 1301, 1160, 1084 cm$^{-1}$ MS nil: 162.1 (M$^+$, 13.6), 120.1 (100.0). 99.1 (79.5), 70.1 (29.2), 56.1 (49.6). HRMS-EI (m/z): [M]$^+$ calculated for, C$_7$H$_{15}$ClN$_2$, 162.0924; found, 162.0930.

(6). Synthesis of Compound-21: (Step 6)

A mixture of succinic anhydride (1.0 eq) and dry alcohol (carbon number is from 2 to 20) (1 eq) in 4 mL toluene was heated at reflux 2.5 hours. The toluene was removed under reduced pressure and the residue was taken up in water, and the solution was extracted with dichloromethane, dried over MgSO$_4$, and evaporated to obtain monoalkylsuccinic acid (carbon number is from 2 to 20).

A solution of monoalkyl succinic acid (carbon number of the alhyl is from 2 to 20) (1.2 eq) and thionyl chloride (1.4 eq) in benzene (5 mL) was refluxed for 3 hours. Subsequently, the majority of the thionyl chloride and benzene were removed by distillation. The mixture was cooled down to room temperature and dried under a vacuum to give a crude chlorocarbony-alkyl ester (carbon number of the alhyl is from 2 to 20). A solution of chlorocarbonyl-alkyl ester (carbon number of the alhyl is from 2 to 20) in 5 mL dichloromethane was added to a round flask containing Compound-5 (1 eq) by cannula, and subsequently added pyridine (1.4 eq). The resulting solution was stirred at room temperature overnight, and quenched by adding water. The solution was extracted with ethyl acetate, dried over MgSO$_4$, and evaporated to give a residue which was purified by column chromatography (Al$_2$O$_3$), eluting by ethyl acetate/hexane (1:15) to provide Compound-21:

dodecyl 4-(4-(3-chloropropyl)piperazin-1-yl)-4-oxobutanoate

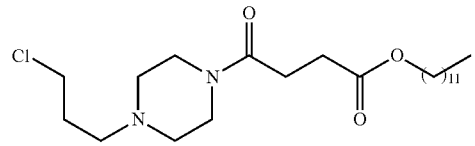

$^1$H NMR (400 MHz, CDCl3, δ): 4.07-4.03 (t, J=6.8 Hz, 2H), 3.60-3.57 (m, 4H), 3.48-3.46 (t, J=4.9 Hz, 2H), 2.65-2.57 (m, 4H), 2.50-2.46 (t, J=6.9 Hz, 2H), 2.44-2.37 (m, 4H), 1.95-1.92 (m, 2H), 1.63-1.57 (m, 2H), 1.34-1.23 (b, 18H), 0.88-0.85 (t, J=6.6 Hz, 3H); 13C NMR (100.6 MHz, CDCl3, δ): 173.2, 169.5, 64.8, 55.1, 53.2, 52.7, 45.2, 42.9, 41.7, 31.9, 29.7, 29.6, 29.5, 29.5, 29.3, 29.2, 29.2, 28.5, 27.8, 25.8, 22.6, 14.0; IR (KBr): 2925, 2854, 1734, 1651, 1444, 1365, 1223, 1169 cm-1. MS m/z: 430.3 (M+, 62.5), 281.1 (11.7), 228.0 (11.7), 221.1 (11.1), 207.1 (18.7), 139.4 (41.3), 60.3 (100.0). HRFAB (m/z): [M]+ calculated for C23H43ClN2O3, 430.2963; found, 430.2954.

(7). Synthesis of SP101: (Step 7)

Compound-4 (1 eq) was dissolved in DMF (1.0 mL), potassium carbonate (2 eq) and Compound-21 (1 eq) were added respectively and heated at 80° C. overnight. The reaction mixture was then cooled to room temperature and quenched by adding water. The resulting solution was extracted with ethyl acetate; the combined extracts were washed with water and brine, dried over MgSO$_4$, and evaporated to give a crude residue which was purified by column chromatography to provide SP101:

dodecyl 4-(4-(3-(4-(3-chloro-4-fluorophenylamino)-7-methoxyquinazolin-6-yloxy)propyl)piperazin-1-yl)-4-oxobutanoate

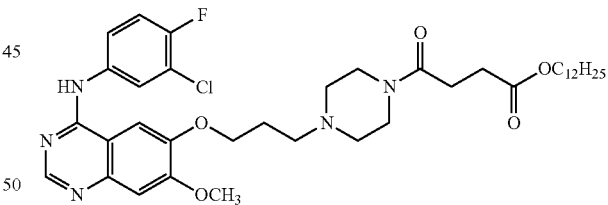

$^1$H NMR (400 MHz, CDCl3, δ): 8.65 (s, 1H), 7.86-7.84 (m, 1H), 7.54-7.51 (m, 2H), 7.24 (s, 1H), 7.17-7.13 (m, 2H), 4.18-4.15 (t, J=6.4 Hz, 2H), 4.07-4.03 (t, J=6.8 Hz, 2H), 3.98 (s, 3H), 3.61 (b, 2H), 3.48 (b, 2H), 2.65-2.56 (m, 6H), 2.48 (b, 2H), 2.44-2.42 (m, 2H), 2.11-2.08 (t, J=6.7 Hz, 2H), 1.61-1.58 (m, 2H), 1.32-1.25 (b, 18H), 0.89-0.85 (t, J=6.7 Hz, 3H). 13C NMR (100.6 MHz, CDCl3, δ): 173.3, 169.8, 156.3, 155.2, 153.5, 153.4, 149.0, 147.4, 135.5, 124.2, 121.8, 121.7, 121.0, 120.8, 116.6, 116.4, 109.0, 107.8, 101.2, 67.5, 64.9, 56.1, 54.7, 53.2, 52.7, 45.1, 41.6, 31.9, 29.6, 29.5, 29.3, 29.2, 28.6, 27.8, 26.2, 25.9, 22.7, 14.1. IR (KBr): 3672, 2925, 2854, 1732, 1625, 1578, 1500, 1470, 1429, 1217 cm-1. MS m/z: 714.3 (M+, 3.4), 551.4 (1.5), 71.7 (49.1), 52.8 (100). HRFAB (m/z): [M]+ calculated for C38H53ClFN5O5, 713.3719; found, 713.3717.

Materials—Antibodies and Cell Lines

Anti-EGFR, anti-p-EGFR (Tyr 1068), anti-cleaved Caspase 3 antibodies were purchased from Cell Signaling, Inc. Anti-Survivin antibody was purchased from Santa Cruz Biotechnology, Inc. Anti-actin antibody was purchased from Millipore. Anti-Nanog and anti-Oct4 antibodies were purchased from Abcam, Inc. Anti-GAPDH, goat anti-rabbit IgG horseradish peroxidase (HRP) and goat anti-mouse IgG horseradish peroxidase (HRP) antibodies were purchased from GeneTex Inc. Anti-rabbit IgG Dylight 488 antibody was purchased from Thermo, Forma. Scientific Inc.

A549 (ATCC number: CCL-185) was a non-small cell lung carcinoma cell line which expressed wild type EGFR and with K-Ras mutation (G12S). H1975 (ATCC number: CRL-5908) was a non-small cell lung carcinoma cell line which expressed EGFR L858R/T790M mutation. Oct4 and Nanog overexpression in A549-ON presented the properties of cancer stem-like cells, as well as epithelial-mesenchymal transdifferentiation. PLC26 was lung cancer cells that separated from pleural effusion of a clinical lung cancer patient (IRB number: 103-011-E). A549-ON cells were cultured in DMEM medium. A549 and H1975 cells were maintained in RPMI-1640 medium. PLC26 cells were maintained in LHC-9 medium. DMEM and RPMI medium were supplemented with 10% fetal bovine serum (FBS), 100 units/ml penicillin, 100 μg/ml streptomycin and sodium bicarbonate. LHC-9 medium was supplemented with 5% FBS and 100 units/ml penicillin. These cells were cultured at 37° C. and 5% $CO_2$ in a humidified incubator.

III. SP101 is More Potent on the Inhibition of Cell Viability of NSCLC Cells with EGFR (T790M) Mutation Please refer to Table 1, which indicates the genotype of EGFR and K-Ras in HFL1 normal lung fibroblast and various human lung cell lines, including A549, A549-ON, H358 and H1975.

Table 1. The Genotype of EGFR and K-Ras in HFL1 Normal Lung Fibroblast and Various Human Lung Cell Lines

TABLE 1

The genotype of EGFR and K-Ras in HFL1 normal lung fibroblast and various human lung cell lines

| Cell lines | EGFR | K-Ras |
| --- | --- | --- |
| HFL1 | Wild-type | Wild-type |
| A549 | Wild-type | G12S |
| A549-ON | Wild-type | G12S |
| H358 | Wild-type | G12S |
| H1975 | L858R/T790M | Wild-type |

Please refer to FIG. 1. The protein levels of EGFR, K-Ras, Oct4 and Nanog in various human lung cell lines were analyzed by Western blot analysis using specific antibodies. Representative immunoblotting data were shown from one of three separate experiments with similar findings. Actin was as an internal control protein. The immunoblot analysis indicated that all cells expressed total EGFR protein. However, H1975 cell line had EGFR L858R and T790M mutation. Furthermore, all cell lines expressed K-Ras protein levels, and NSCLC cells expressed more Survivin level than normal lung fibroblast HFL1. In addition, Oct4 and Nanog play critical roles in survival of cancer drug-resistant cells enriched for cancer stem cells. A549-ON is, lung cancer stem-like cell which expressed cancer stem cell markers Oct4 and Nanog proteins. HFL1, A549, H358 and H1975 cells also expressed Nanog protein level but did not express Oct4 protein level.

Figure 2:
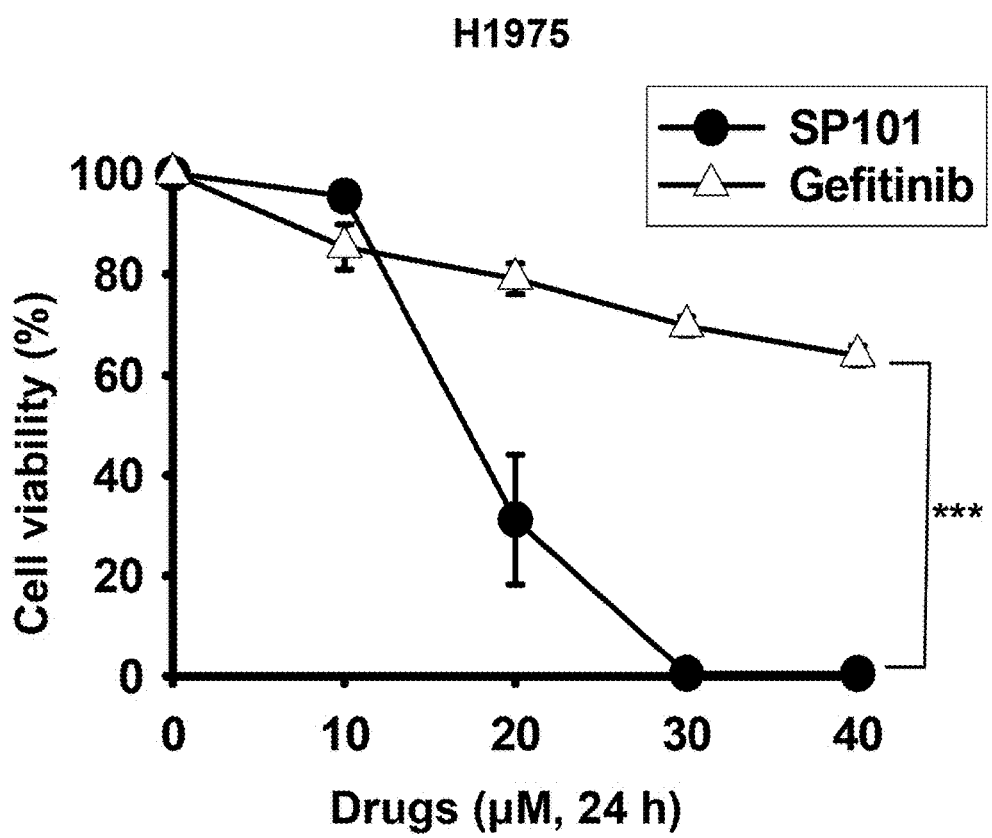
FIG. 2 shows comparison of SP101 and Gefitinib in the reduction of cell viability in the H1975 lung cancer cells.

Please refer to FIG. 2. The H1975 cells were treated with 0~40 μM of SP101 or Gefitinib for 24 hours. After treatment, the H1975 cells were re-cultured in fresh medium for 2 days. The cell viability was analyzed by MTT assays. The results were obtained from three independent experiments and the var represents the mean±S.E.M. ***$p<0.001$ indicates significant difference between Gefitinib and SP101 treated samples. The cell viability inhibition in H1975 cells was significantly higher in the SP101 group than in the Gefitinib group. SP101 is more effective on the ability to reduce the drug resistance of EGFR (T790M) than Gefitinib in NSCLC.

Figure 3:
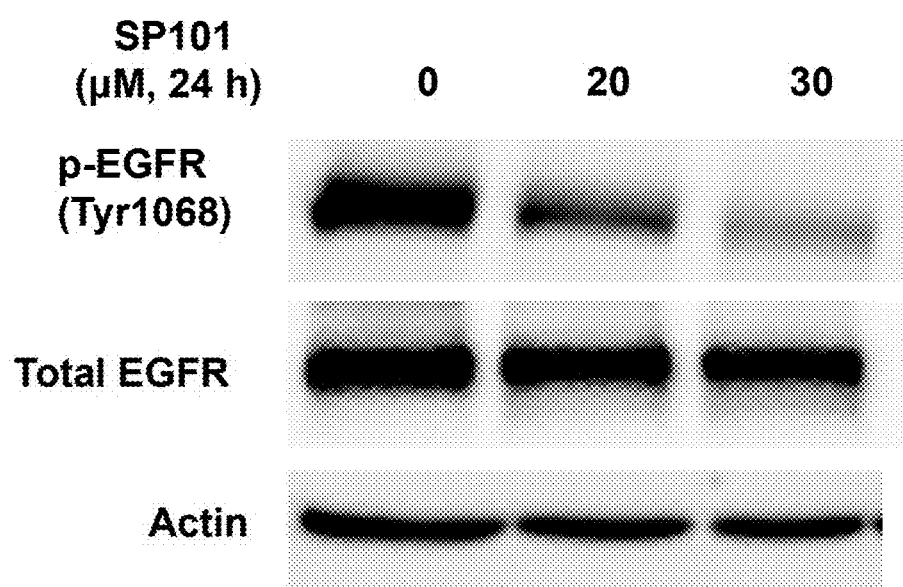
FIG. 3 shows Western blot analysis result of phosphorylated EGFR (Tyr 1068) and total EGFR proteins in H1975 cells with EGFR (T790M) mutation after SP101 treatment.

IV. SP101 Inhibits Protein Level of Phosphorylated EGFR in NSCLC Cells with EGFR (T7901M) Mutation EGFR binding cognate ligands may lead to autophosphorylation of receptor tyrosine kinase and subsequent activation of signal transduction pathways of cell survival. Besides, aberrant tyrosine kinase activation increases proliferation and drug resistance of malignant cells. Please refer to FIG. 3. H1975 cells were treated with 0~30 μM of SP101 for 24 hours. The total protein extracts were prepared for Western blot analyses using specific antibodies, including rabbit anti-p-EGFR (Tyr1068), rabbit anti-EGFR and mouse anti-actin. Representative immunoblotting data were shown from one of three separate experiments with similar findings. Actin was an internal control protein. SP101 (20~30 μM for 24 hours) significantly reduced the phosphorylated EGFR (Tyr 1068) protein level but did not inhibit total EGFR protein level.

Figure 4:
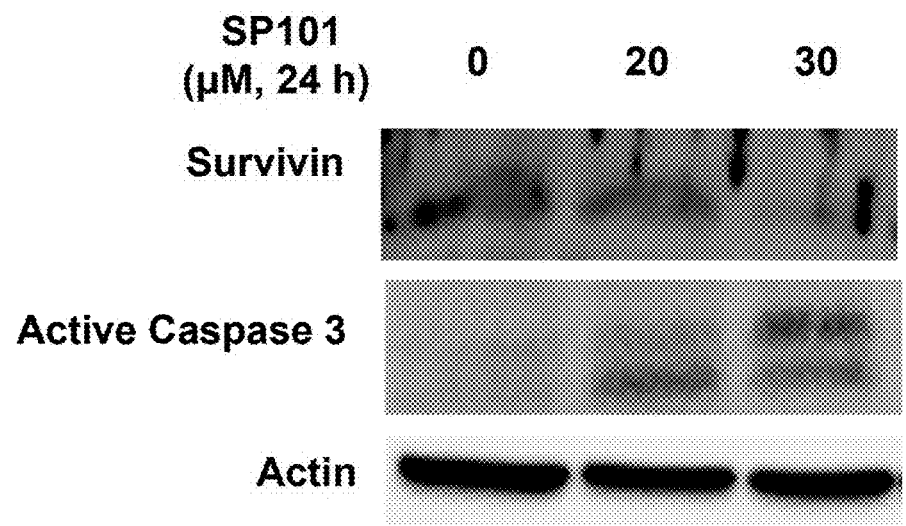
FIG. 4 shows Western blot analysis result of expression of Survivin protein and apoptotic Caspase 3 proteins after treatment with or without SP101 in H1975 cells with EGFR (T790M) mutation.

V. SP101 Reduces Protein Level of Survivin and Increases Active Caspase 3 Protein in NSCLC Cells with EGFR (T790M) Mutation Survivin protein has been suggested to involve in tumorigenesis through diverse mechanisms, including prevent caspase-mediated cell death and regulate cell cycle. Reduction of Survivin protein expression has shown to inhibit tumor growth in NSCLC. Please refer to FIG. 4. H1975 cells with EGFR (T790M) mutation were treated with or without SP101 (20~30 μM for 24 hours) and analyzed by Western blot. The Western blot result indicated that SP101 reduced Survivin protein level; moreover apoptotic protein level of cleaved-form Caspase 3 was induced. Actin was an internal control protein.

Figure 5:
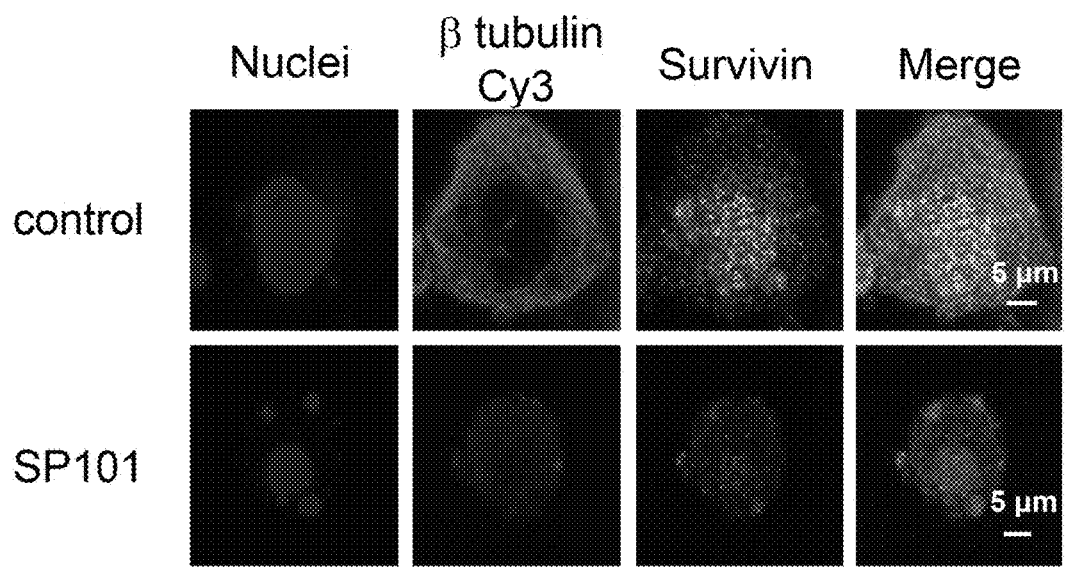
FIG. 5 is a result of immunofluorescence staining and confocal microscopy. The green color indicated location of Survivin protein excited with 488 nm. The β-tubulin protein was stained with Cy3-labeled mouse anti-β-tubulin antibody (red color). The fluorescence intensity of β-tubulin was excited with 543 nm and the emission was collected in range of 560-580 nm. Blue color indicated location of nuclei following stained with Hoechst 33258 and was excited with 405 nm and the emission was collected in range of 415-450 nm. Overlapping localization is shown in the merged images.
Figure 6:
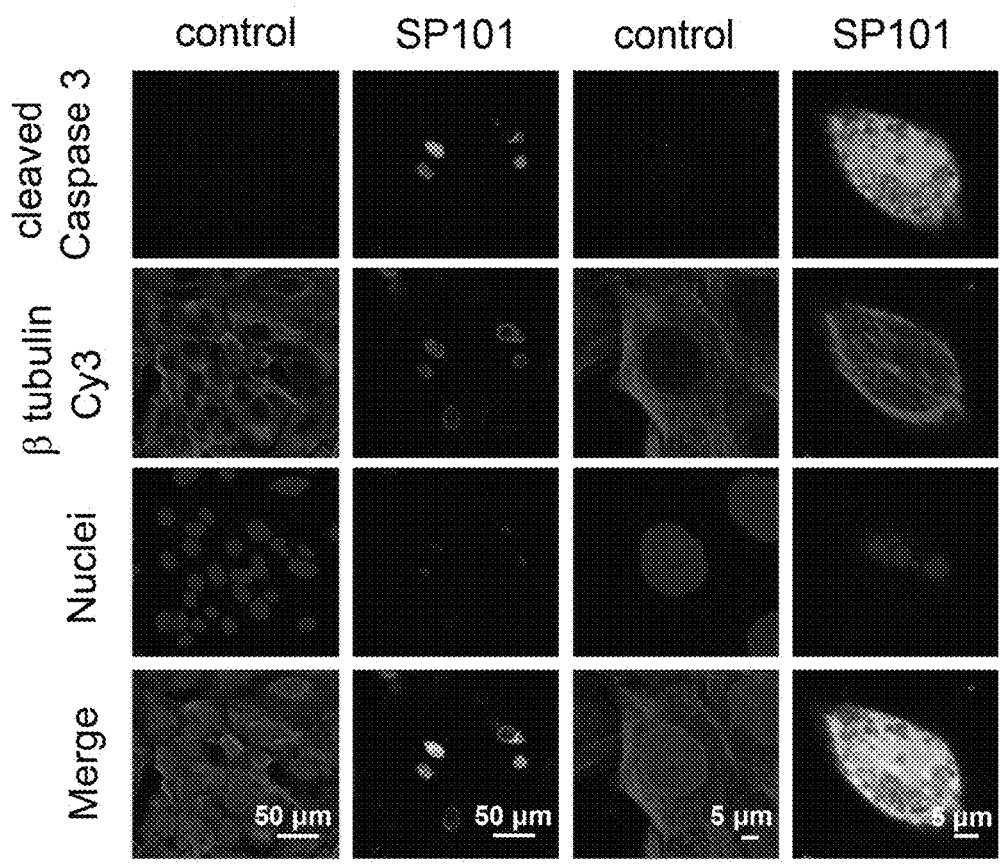
FIG. 6 is a result of immunofluorescence staining and confocal microscopy. The green color indicated location of cleaved Caspase 3 protein excited with 488 nm. The β-tubulin protein was stained with Cy3-labeled mouse anti-β-tubulin antibody (red color). The fluorescence intensity of β-tubulin was excited with 543 nm and the emission was collected in range of 560-580 nm. Blue color indicated location of nuclei following stained with Hoechst 33258 and was excited with 405 nm and the emission was collected in range of 415-450 nm. Overlapping localization is shown in the merged images.

Further, immunofluorescence staining and confocal microscopy were utilized to determine the expression and cell morphology of Survivin and cleaved-form Caspase 3 after treatment with SP101 in H1975 cells with EGFR (T790M) mutation. The cells were treated with or without 30 μM of SP101 for 24 hours. At the end of treatment, the cells were fixed with 4% paraformaldehyde at 37□C for 1 hour. The fixed cells were incubated with rabbit anti-Survivin antibody or rabbit anti-cleaved caspase-3 antibody at 4□C overnight. Then the cells were stained with goat anti-rabbit IgG Dylight 488 at 37□C for 1 hour. Please refer to FIGS. 5 and 6. The green fluorescence (Dylight 488) indicated location of Survivin and cleaved-form Caspase 3. The blue fluorescence (Hoechst 33258) and red fluorescence (Cy3) represented nucleus and β-tubulin respectively. Treatment with 30 μM SP101 for 24 hours, Survivin protein expression was reduced; in addition, the apoptotic bodies and cleaved-form Caspase 3 protein were induced. These findings demonstrated that SP101 reduced protein level Survivin and increased active Caspase 3 protein for apoptosis induction in the Gefitinib-drug resistant H1975 cells. Hence, the present application suggests that SP101 may overcome drug resistance of EGFR (T790M) in human NSCLC.

Figure 7:
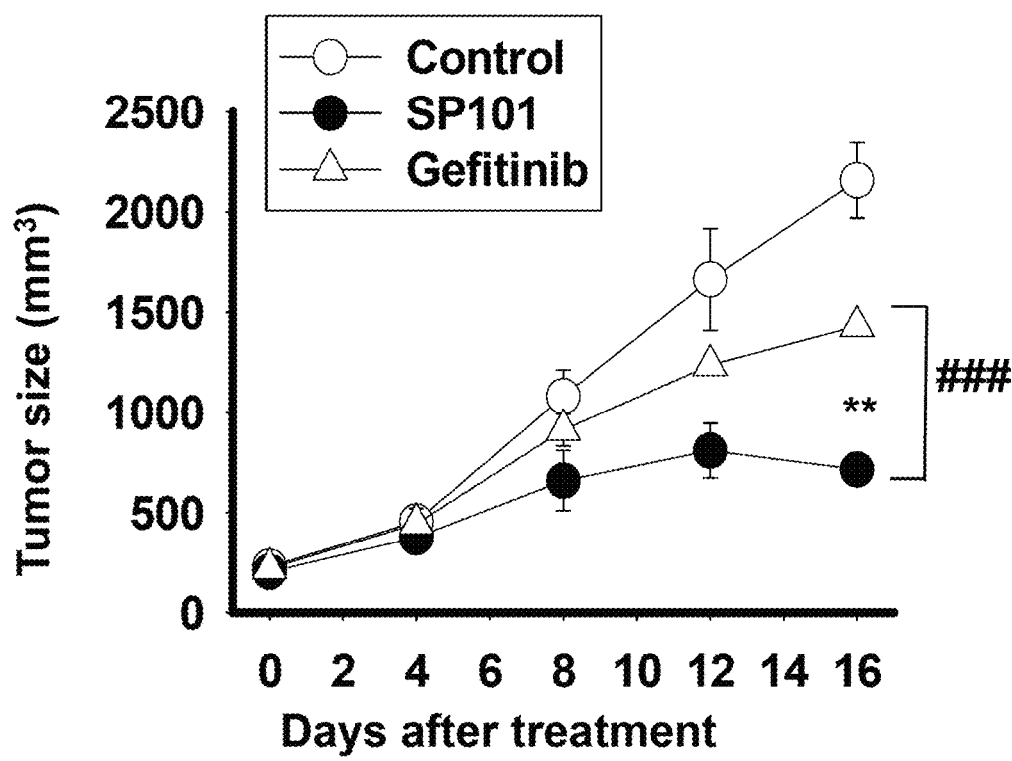
FIG. 7 shows tumor sizes measured every four days in the xenografted human NSCLC tumors nude mice. The results were obtained from twelve mice and the bar represents the mean±S.E.M.**p<0.01, indicating significant difference between control and SP101 treatment group mice. ###p<0.001 indicates significant differences between SP101 and Gefitinib-treated mice.
Figure 8:
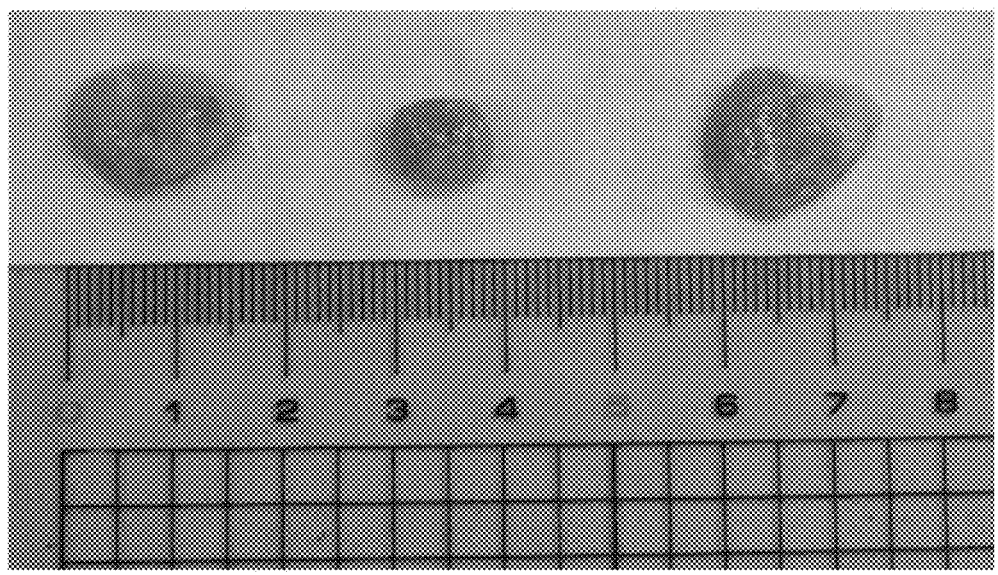
FIG. 8 shows the actual tumor sizes in the xenografted human NSCLC tumors nude mice after vehicle, SP101 or Gefitinib treatment for 16 days.
Figure 9:
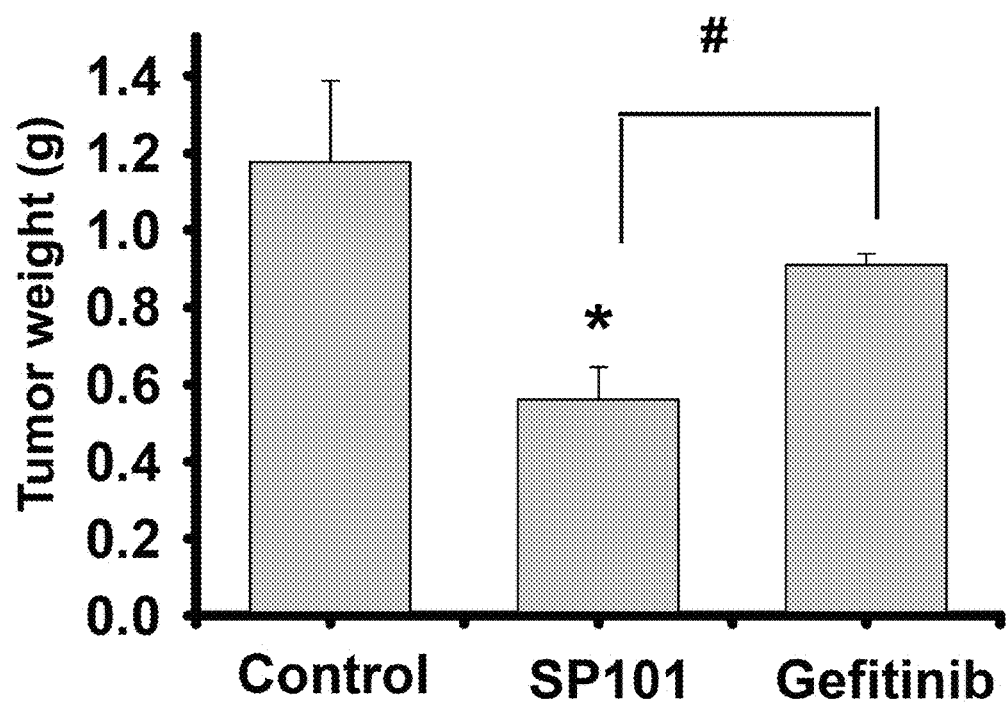
FIG. 9 shows tumor weights measured after sacrificing the xenografted human NSCLC tumors nude nice. The tumor weight was means±*p<0.05 indicating significant differences between control and SP101 treatment group mice. #p<0.05 indicates significant differences between SP101 and Gefitinib-treated mice.

VI. SP101 Enhances Inhibition of Tumor Growth in the Xenografted Human NSCLC Model with EGFR (T790M) Mutation To compare the antitumor activity of SP101 and Gefitinib, the xenografted human NSCLC tumors in nude mice were established. Seven-week-old nude mice were subcutaneously injected with $3 \times 10^6$ H1975 cells. Please refer to FIGS. 7 and 8. After 7 to 10 days inoculation, the nude mice were treated with vehicle or 30 mg/kg SP101 or 30 mg/kg Gefitinib once per four days and tumor sizes in the nude mice were measured every four days. The nude mice were sacrificed after treatment for 16 days; the tumors were harvested to measure tumor volume/weight and further analyze tumor tissues. SP101 significantly inhibited the tumor growth in the nude mice. Please refer to FIG. 9. The tumor weight was measured after sacrifice and it showed that treatment with SP101 was more potent on the inhibition of tumor weight than Gefitinib. However, these treatments did not alter body weight of the nude mice during the treatment period.

Figure 10:
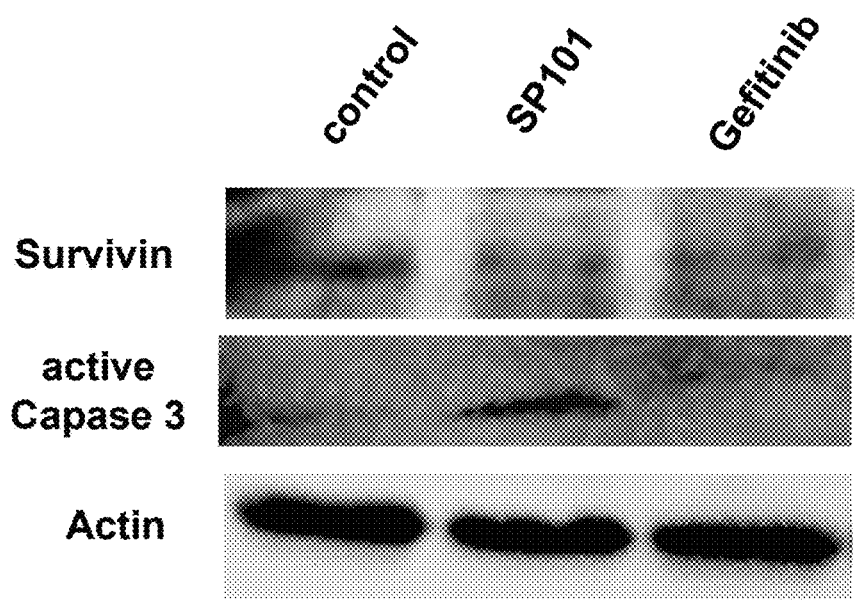
FIG. 10 shows SP101 reduced Survivin protein and increased active Caspase 3 in the tumor tissues of xenografted human NSCLC in nude mice.

VII. SP101 Reduces Survivin Protein and Increases Active Caspase 3 Protein in the Tumor Tissues of Xenografted Human NSCLC in the Nude Mice with EGFR (T790M) Mutation Please refer to FIG. 10. The xenograft tumor tissues from each group were homogenized and the total lysates were subjected to Western blot analysis using specific antibodies, including rabbit anti-Survivin, rabbit anti-cleaved Caspase 3 and mouse anti-actin. Representative immunoblotting data were shown from one of two separate experiments with similar findings. Actin was an internal control protein. SP101 reduced Survivin protein level; meanwhile, SP101 induced the apoptotic protein level of cleaved Caspase 3. Sp101 is more potent on the reduction of Survivin protein and increasing of cleaved Caspase 3 protein level than Gefitinib in the xenograft tumor tissues.

Figure 11:
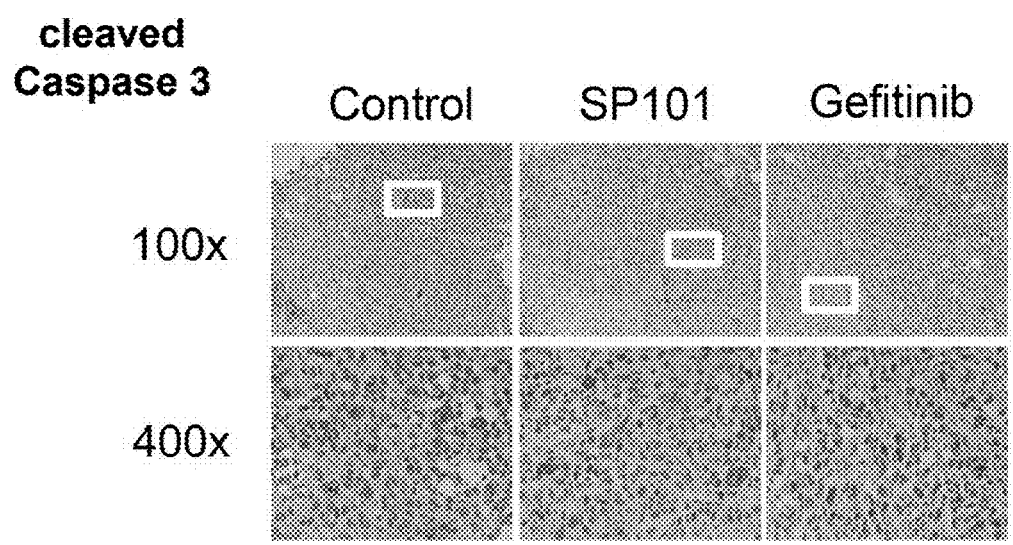
FIG. 11 is a result of IHC immunohistochemistry staining showing that SP101 enhanced Caspase 3 protein level in NSCLC tumor tissues. Representative photographs were by IHC staining the active Caspase 3 proteins in the tumor sections. Positive cells were visualized by DAB staining (brown), counterstain with nuclei by hematoxylin.

Please refer to FIG. 11. The histologicalanalysis utilized IHC staining to compare with control and Gefitinib groups, SP101 significantly induced the active forms of Caspase 3 protein in the immunohistochemistry staining from the xenografted NSCLC tumors.

These findings demonstrated that SP101 decreases Survivin protein but conversely increases active Caspase 3 protein for apoptosis induction to block tumor growth in NSCLC.

Figure 12:
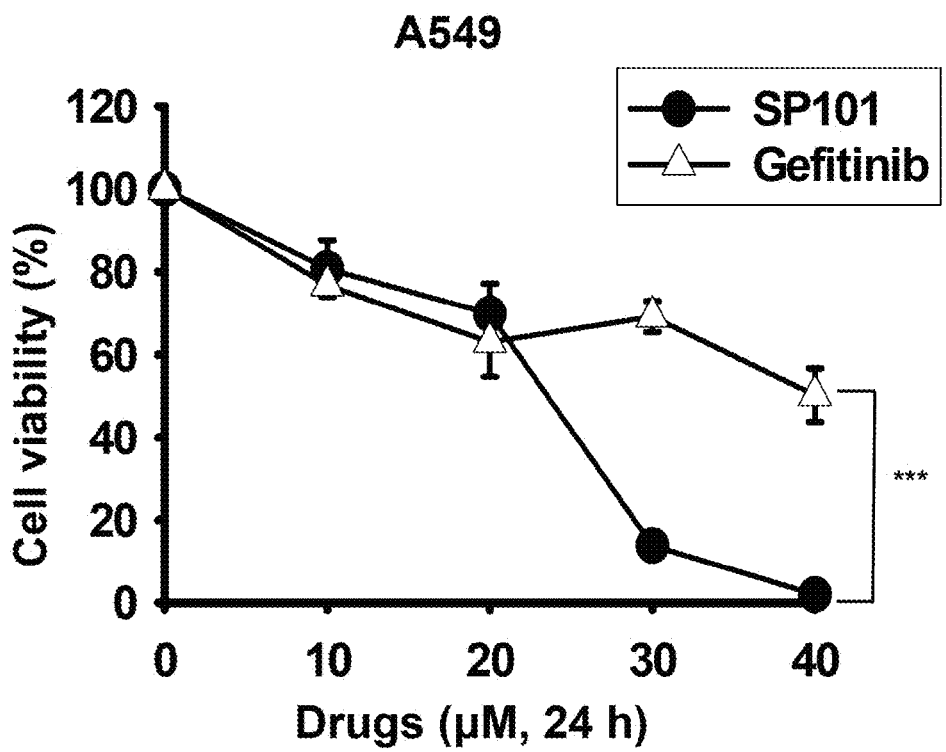
FIG. 12 shows that A549 cells were treated with 0~40 μM of SP101 or Gefitinib for 24 hours. After treatment, the cells were re-cultured in fresh medium for 2 days. The cell viability was analyzed by MTT assays. The results were obtained from three independent experiments and the bar represents the mean±S.E.M. ***p<0.001 indicates significant difference between Gefitinib and SP101 treated samples.
Figure 13:
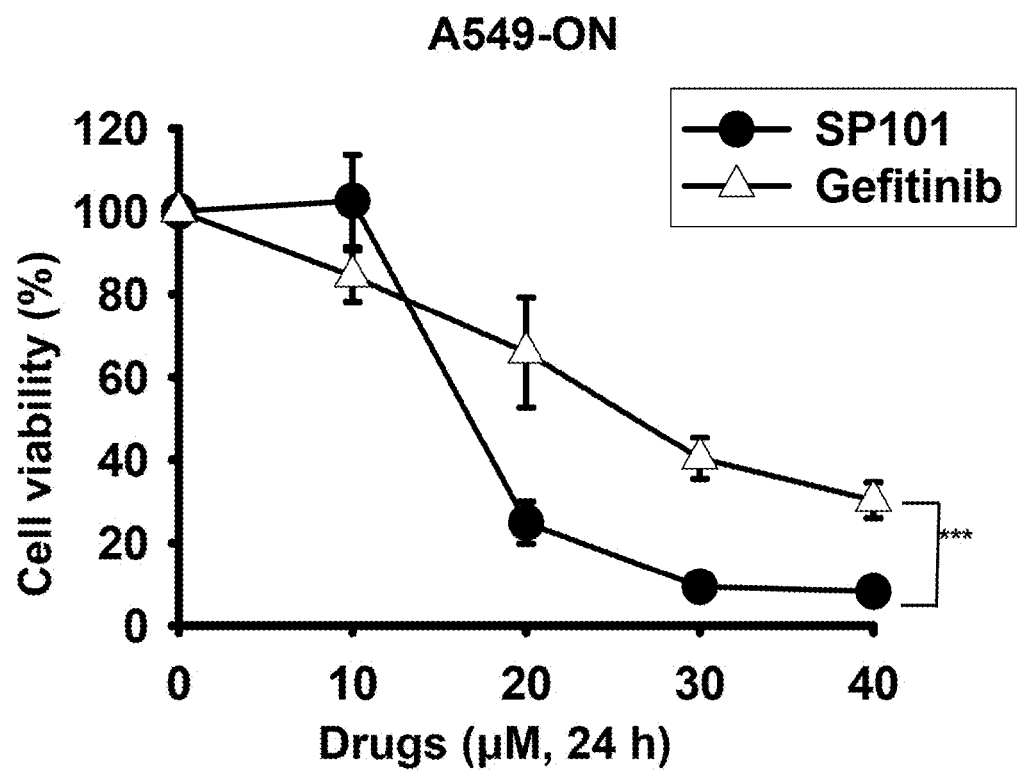
FIG. 13 shows that A549-ON cells were treated with 0~40 μM of SP101 or Gefitinib for 24 hours. After treatment, the cells were re-cultured in fresh medium for 2 days. The cell viability was analyzed by MTT assays. The results were obtained from three independent experiments and the bar represents the mean±S.E.M. ***p<0.001 indicates significant difference between Gefitinib and SP101 treated samples.

VIII. SP101 is More Potent on the Reduction of Cell Viability than Gefitinib in NSCLC Cells with K-Ras Mutation Please refer to FIG. 12. K-Ras is one of most commonly mutated oncogene in NSCLC, and K-Ras mutation is associated with resistance to Gefitinib. Cancer stem cells are associated with resistance to Gefitinib in NSCLC. To compare the cell viability of SP101 and Gefitinib in K-Ras mutation-drug resistant A549 and A549-ON cell lines, the cells were treated with 0~40 µM SP101 or Gefitinib for 24 hours, and analyzed by MTT assays. SP101 was more potent on the reduction of cell viability than Gefitinib in the A549 lung cancer cells. Please refer to FIG. 13. To determine the effect of SP101 and Gefitinib on the cell viability in cancer stem-like A549-ON cells, the cells were treated with 10~40 µM SP101 or Gefitinib for 24 hours, and analyzed by MTT assays. Treatment of SP101 significantly reduced the cell viability via a concentration-dependent manner in the A549-ON cells. We have demonstrated that SP101 can overcome the drug resistance of stemness property of NSCLC.

Figure 14:
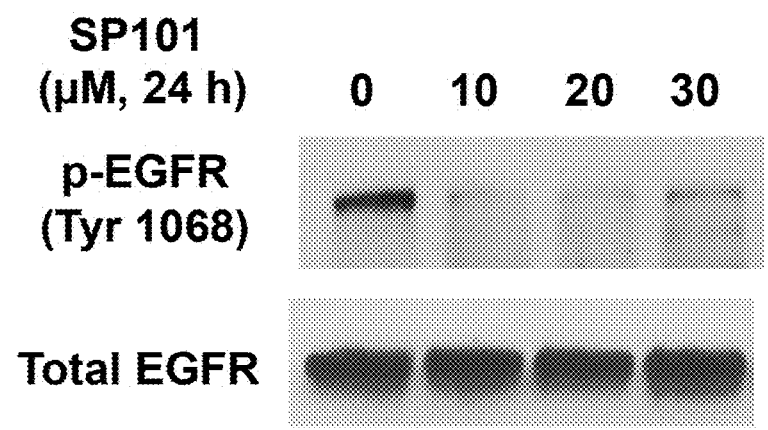
FIG. 14 shows that the cells cells were treated with 0~30 μM of SP101 for 24 hours. At the end of treatment, the total protein extracts were prepared for Western blot analyses using specific antibodies, including rabbit anti-p-EGFR (Tyr1068), rabbit anti-EGFR and mouse anti-actin. Representative immunoblotting data were shown from one of three separate experiments with similar findings. Actin was an internal control protein.
Figure 15:
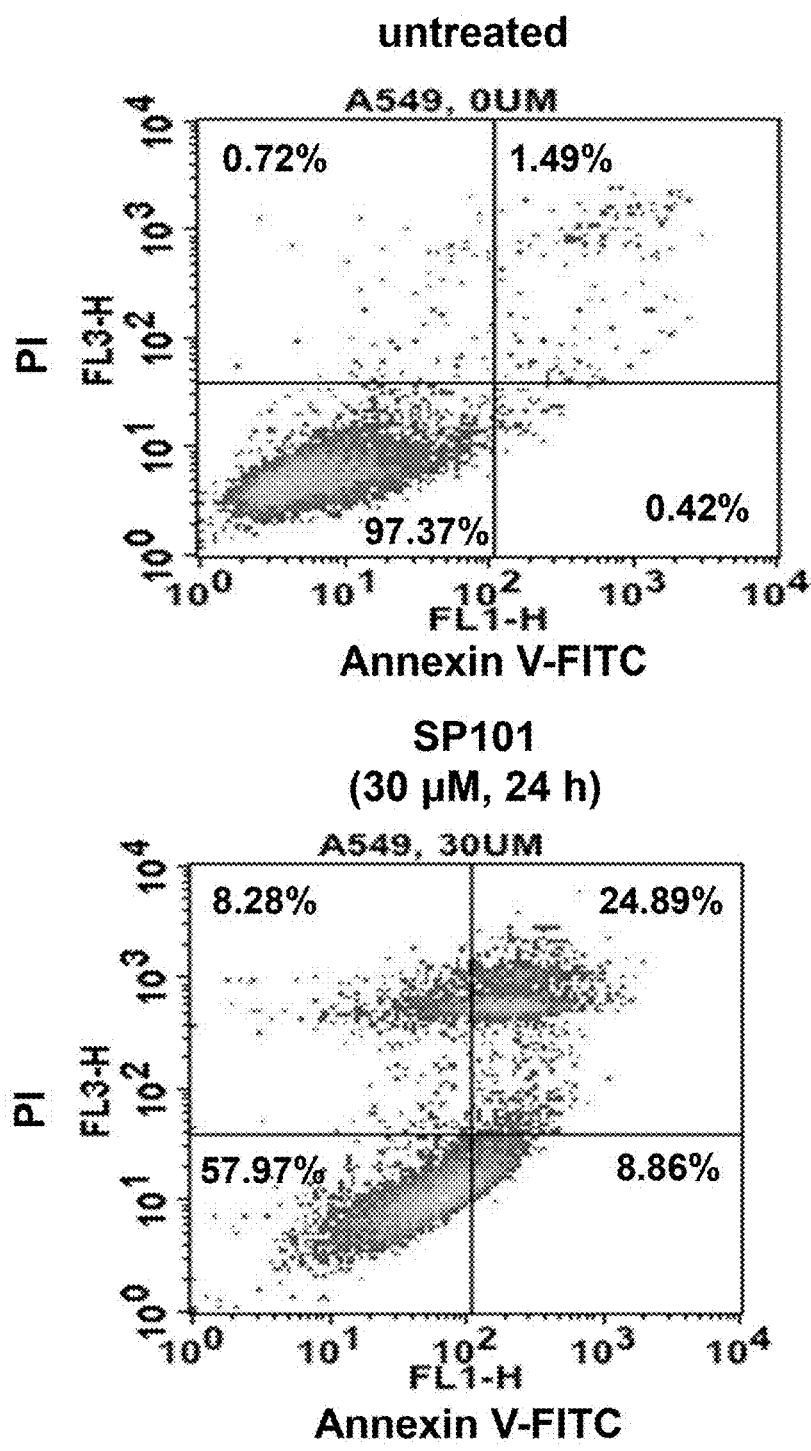
FIG. 15 shows that the cells were treated with or without 30 μM of SP101. At the end of treatment, apoptosis was measured by Annexin VPI staining using flow cytometry analysis. The population of Annexin V+/PI− cells represents cells undergoing early apoptosis (low right), whereas the fraction of Annexin V+/PI+ cell are those undergoing late apoptosis (upper right). The representative flow data were shown from one of three separate experiments with similar findings.

IX. SP101 Inhibits Protein Level of Phosphorylated EGFR in NSCLC Cells with K-Ras Mutation and Induces Apoptosis Please refer to FIG. 14. The expressions of phosphorylated EGFR and total EGFR proteins after treatment with SP101 (10~40 µM for 24 hours) in the K-Ras mutation A549 cells were analyzed by Western blot. We found that SP101 significantly reduced phosphorylated EGFR (Tyr1068) protein levels. Moreover, total EGFR protein levels did not alter by SP101. Please refer to FIG. 15. We further examined the apoptosis levels of SP101 in A549 cells by Annexin V and PI staining. The cells were trypsinized and then incubated with propidium iodide (5 µl) and Annexin V-FITC (5 µl) at room temperature for 5 min before flow cytometry. The levels of Annexin V+/PI– cells (early apoptosis) and Annexin V+/PI+ cells (late apoptosis) were significantly increased by treatment with SP101 at 30 µM for 24 hours in A549 cells.

Figure 16:
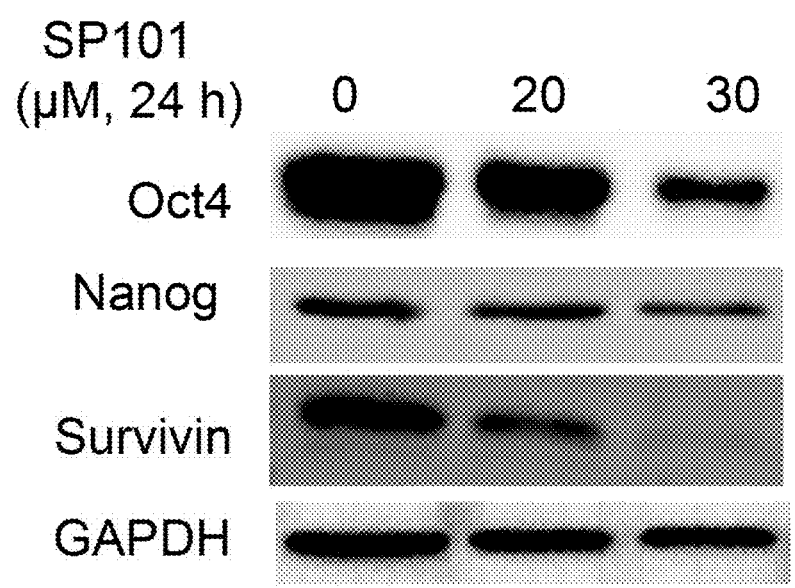
FIG. 16 shows that the A549-ON cells were treated with 0~30 μM of SP101 for 24 hour. At the end of treatment, the total protein extracts were prepared for Western blot analyses using specific antibodies, including rabbit anti-Survivin, rabbit anti-cleaved caspase 3 and mouse anti-actin. Representative immunoblotting data were shown from one of three separate experiments with similar findings. GAPDH was an internal control protein.
Figure 17:
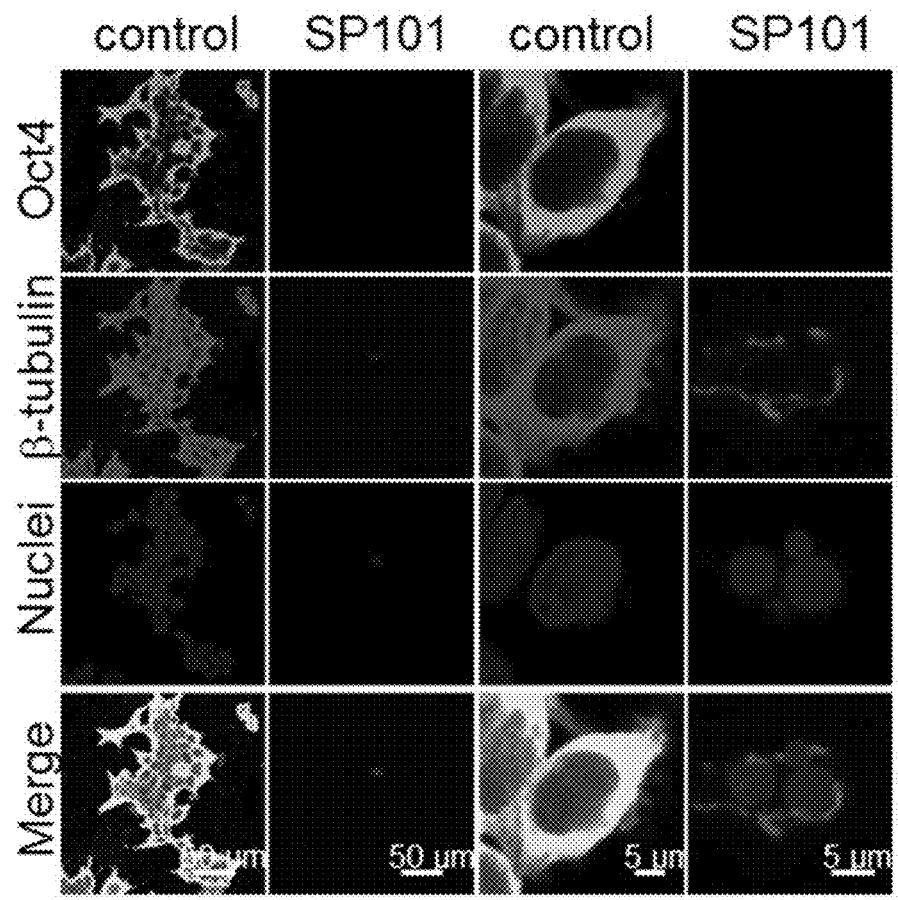
FIG. 17 is a result of immunofluorescence staining and confocal microscopy. Then green color indicates the location of Oct4 excited with 488 nm and the emission and collected in 493-518 nm. The β-tubulin was stained with Cy3-labeled mouse anti-β-tubulin antibody. The fluorescence intensity of β-tubulin (red color) was excited with 543 nm and the emission was collected in range of 560-580 nm. Blue fluorescence indicates nuclei following staining with Hoechst 33258 and was excited with 405 nm and the emission was collected in 415-450 nm. Overlapping localization is shown in the merged images.
Figure 18:
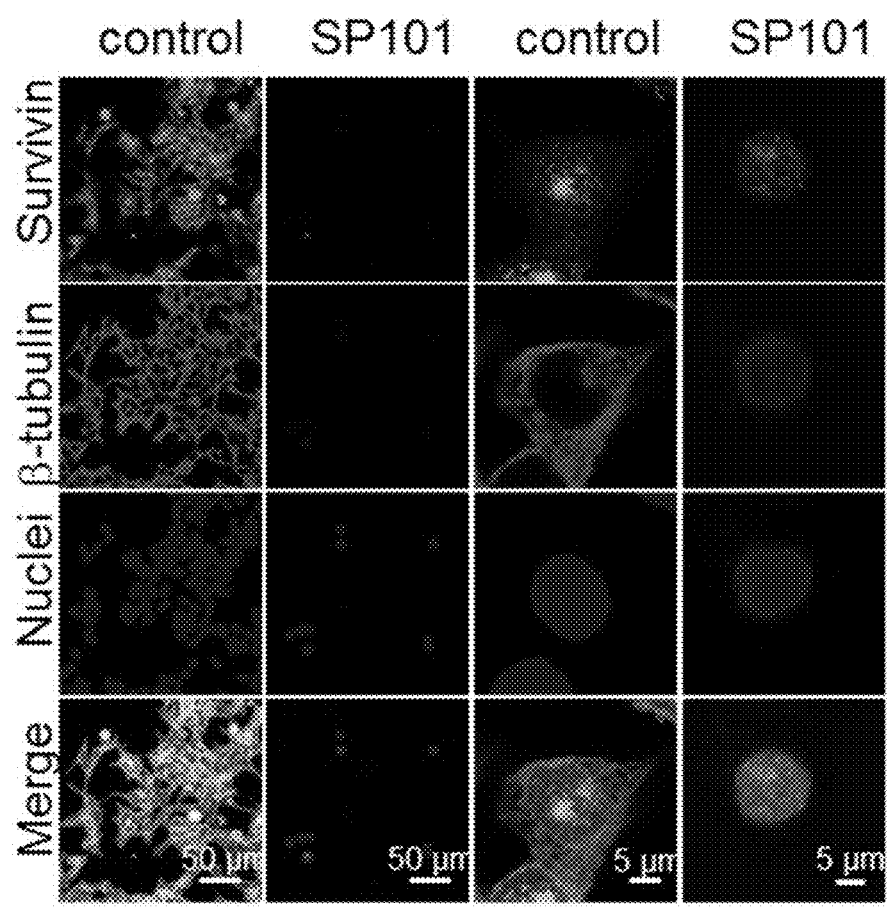
FIG. 18 is a result of immunofluorescence staining and confocal microscopy. Then green color indicates the location of Survivin protein excited with 488 nm and the emission and collected in 493-518 nm. The β-tubulin was stained with Cy3-labeled mouse anti-β-tubulin antibody. The fluorescence intensity of β-tubulin (red color) was excited with 543 nm and the emission was collected in range of 560-580 nm. Blue fluorescence indicates nuclei following staining with Hoechst 33258 and was excited with 405 nm and the emission was collected in 415-450 nm. Overlapping localization is shown in the merged images.

X. SP101 Inhibits Protein Levels of Oct4 Nanog and Survivin its NSCLC Cells with Cancerous Stemness Oct4 and Nanog have been served as markers of tumorigenesis. Furthermore, Oct4 played a pivotal role in Gefitinib resistance in lung cancer stem cells. Oct4 was demonstrated that regulated Survivin protein expression in cancers. Please refer to FIG. 16. We found that the proteins expression of Oct4, Nanog and Survivin were significantly reduced following treatment with 20<30 µM SP101 for 24 hours in A549-ON cells. We further investigated the expression of Oct4 and Survivin by immunofluorescence staining and confocal microscopy. Please refer to FIGS. 17 and 18. The green fluorescence (dylight 488) indicated the location of Oct4 and Survivin. The blue fluorescence (Hoechst 33258) and red (Cy3) fluorescence represent nucleus and β-tubulin, respectively. Treatment with 30 µM SP101 for 24 hours inhibited Oct4 proteins expression and induced apoptotic bodies as shown in FIG. 17; moreover, the Survivin proteins were inhibited by SP101 treatment as shown in FIG. 18. The results demonstrate that SP101 inhibits Oct4 and Survivin protein for apoptotic induction in the A549-ON cells.

Figure 19:
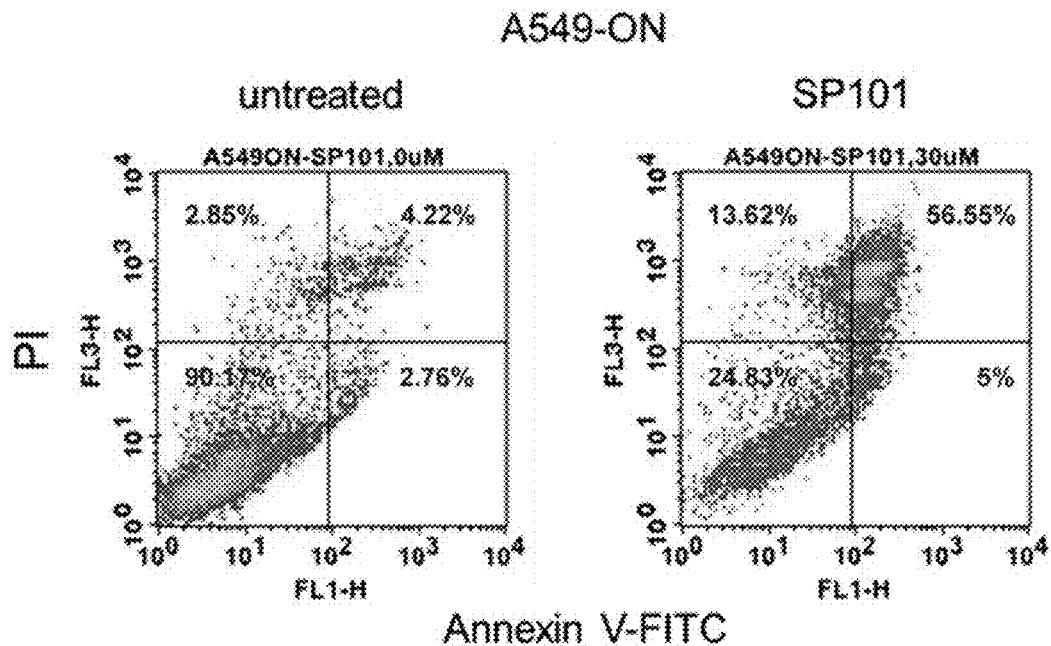
FIG. 19 shows that the cells were treated with or without 30 μM of SP101 and Gefitinib. At the end of treatment, apoptosis was measured by Annexin V-PI staining using flow cytometry analysis. The population of Annexin V+/PI− cells represents cells undergoing early apoptosis (low right), whereas the fraction of Annexin V+/PI+ cell are those undergoing late apoptosis (upper right). The representative flow data were shown from one of three separate experiments with similar findings.
Figure 19:
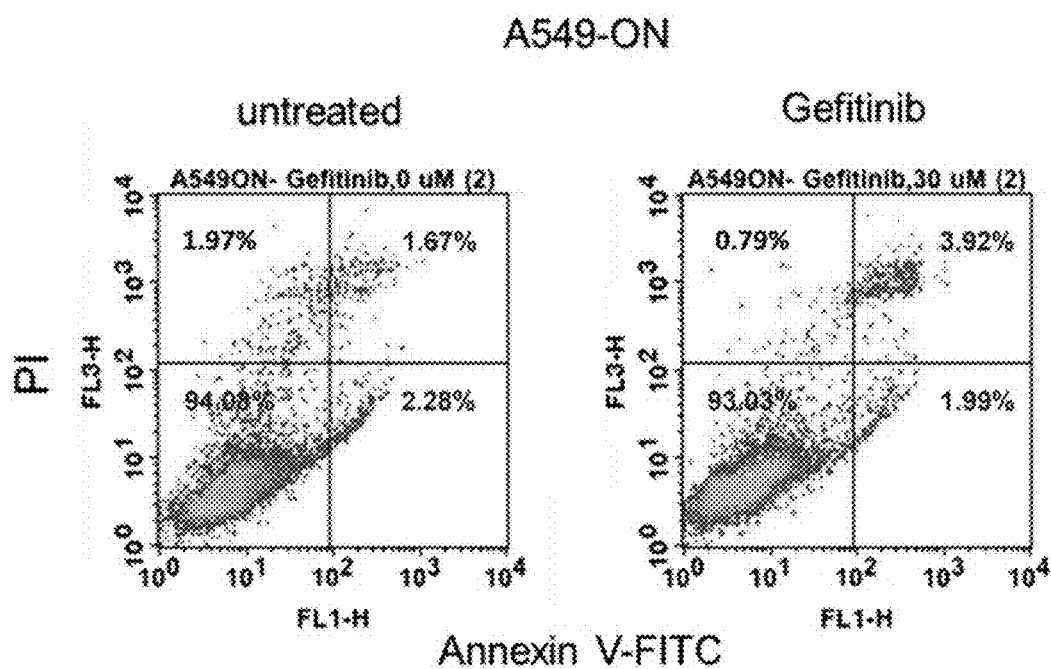
Figure 20:
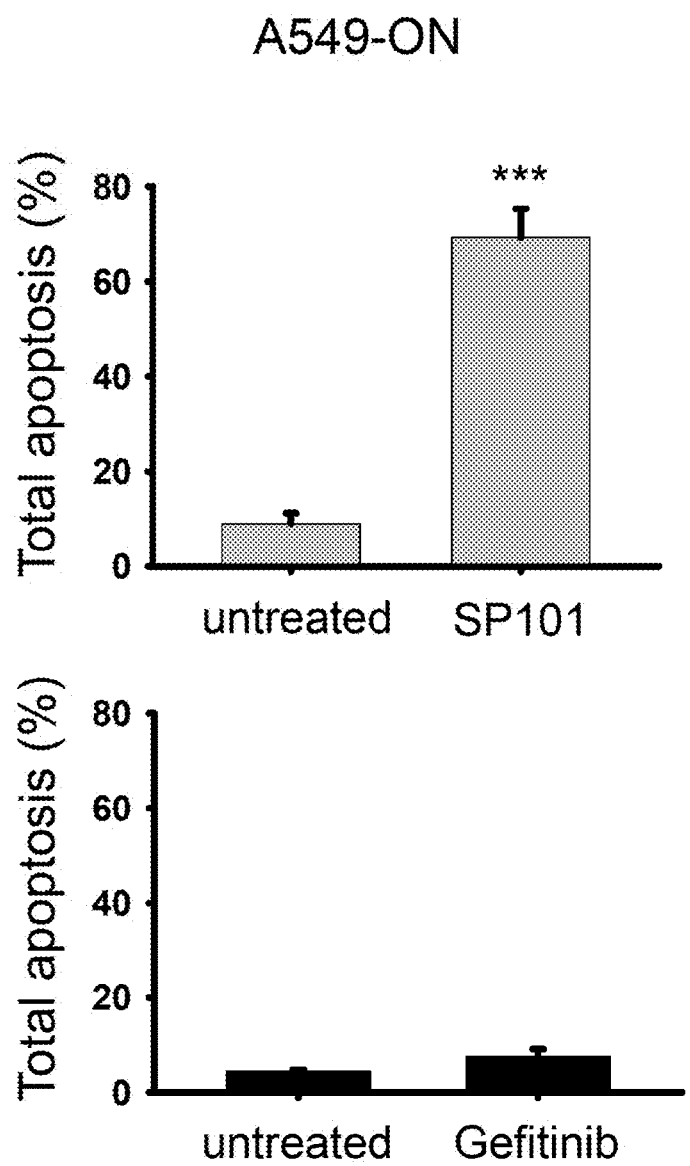
FIG. 20 shows the populations of total apoptotic cells including early and late apoptosis quantified by CellQuest software in flow cytometry. The bar represents the mean±S.E.M. ***p<0.001 indicates significant difference between untreated and SP101 or Gefitinib treated samples.

XI. SP101 is More Potent on Apoptosis Induction than Gefitinib in NSCLC Cells with Cancerous Stemness We compared the apoptosis levels of SP101 and Gefitinib in cancer stem-like A549-ON cells by Annexin V and PI staining. Please refer to FIG. 19. The levels of Annexin V+/PI– cells (early apoptosis) and Annexin V+/PI+ cells (late apoptosis) were significantly increased by treatment with SP101 30 µM in A549-ON cells. Treatment with 30 µM of SP101 induced more late apoptosis cells than Gefitinib. Please refer to FIG. 20. The average of total apoptosis follows SP101 and Gefitinib in the A549-ON cells around 69.29% and 7.59%, respectively.

Figure 21:
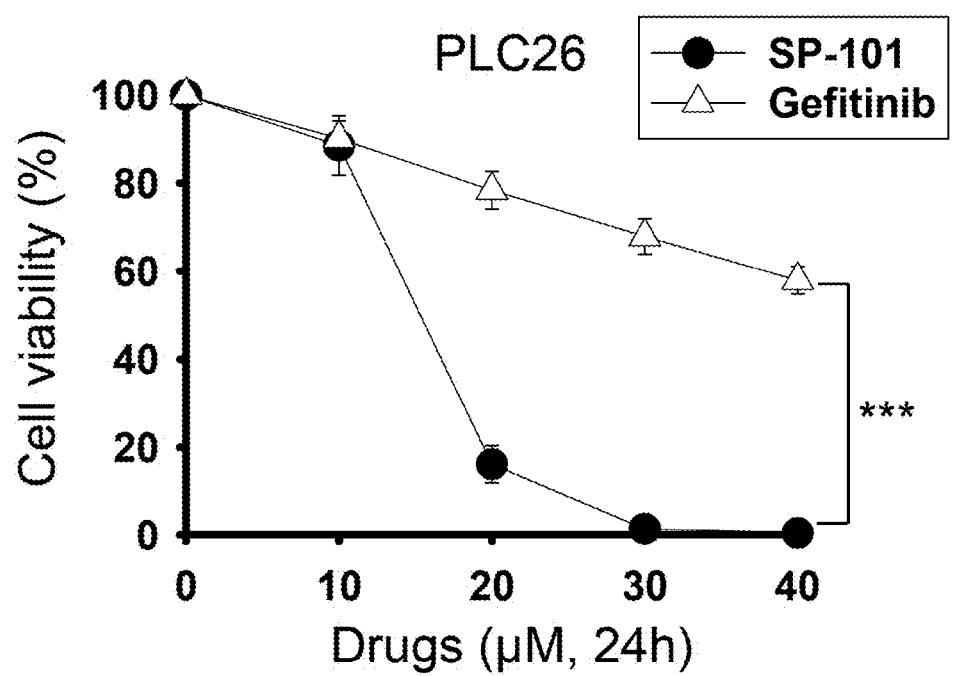
FIG. 21 shows that PLC26 cells were treated with or without 10~40 μM of SP101 or Gefitinib for 24 hours. After treatment, the cells were re-cultured in fresh medium for 2 days. The cell viability was analyzed by MTT assays. The results were obtained from three independent experiments and the bar represents the mean±S.E.M. ***p<0.001 indicates significant difference between gefitinib and SP101 treated samples.
Figure 22:
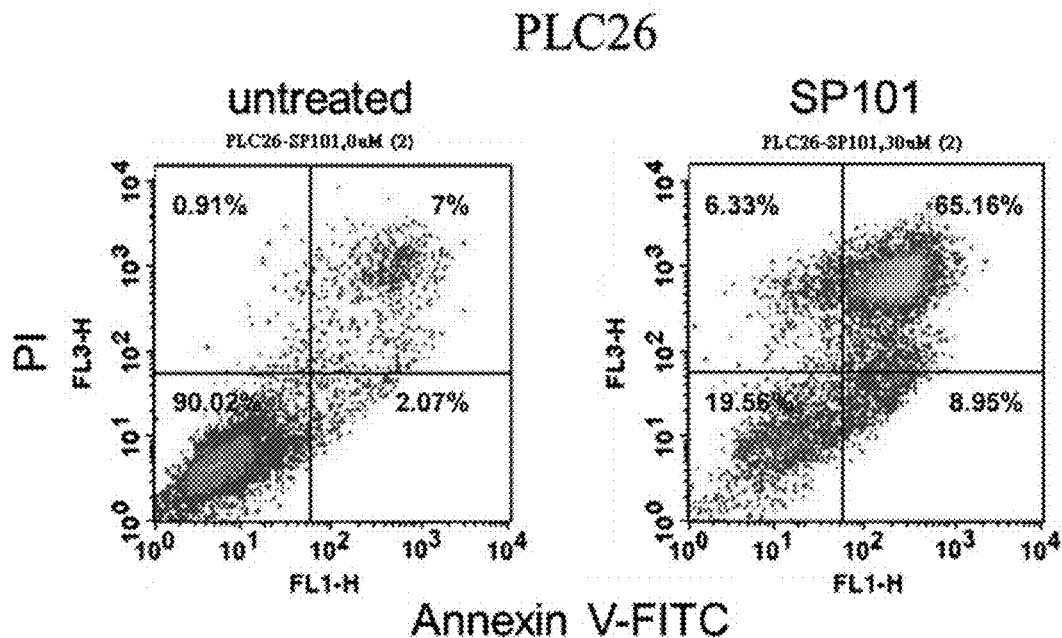
FIG. 22 shows that PLC26 cells were treated with or without 30 μM of SP101 or Gefitinib for 24 hours. At the end of treatment, apoptosis was measured by Annexin V-PI staining using flow cytometry analysis. The population of Annexin V+/PI− cells represents cells undergoing early apoptosis (low right), whereas the fraction of Annexin V+/PI+ cell are those undergoing late apoptosis (upper right).
Figure 22:
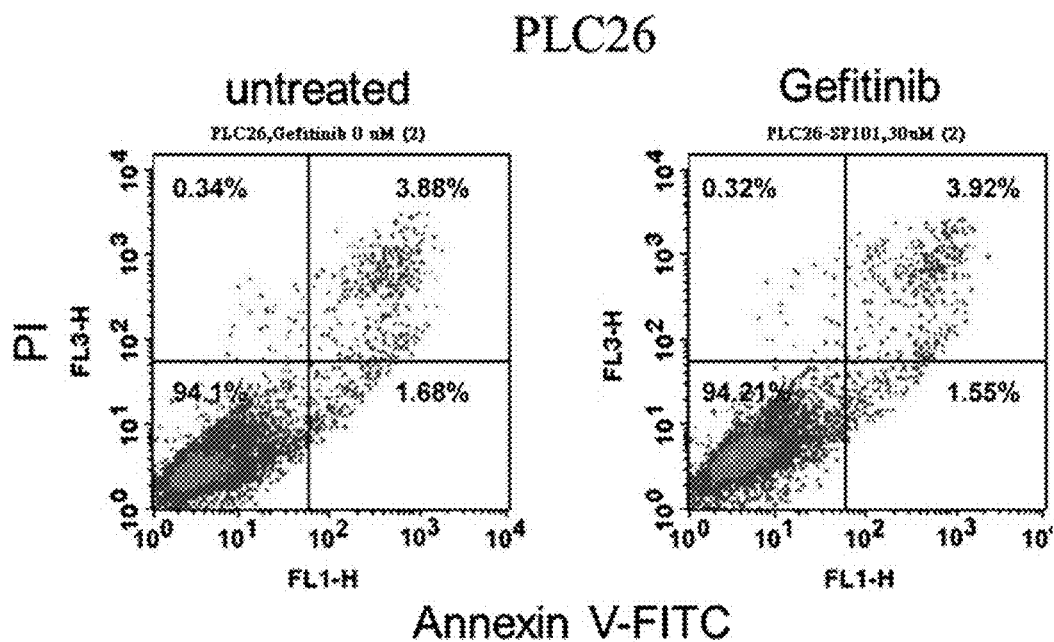

XII. SP101 is More Effective on the Reduction of Cell Viability than Gefitinib in the PLC26 Lung Cancer Cells Separated from the Pleural Effusion of a Clinical Lung Cancer Patient We have further investigated the effect of SP101 in PLC26 lung cancer cells separated from the pleural effusion of a clinical lung cancer patient. To compare the cell viability of SP101 and Gefitinib in PLC26 cells, the cells were treated with 0~40 µM SP101 or Gefitinib for 24 hours, and analyzed by MTT assays. Please refer to FIG. 21. SP101 was more effective on the reduction of cell viability than Gefitinib in the PLC26 cells. The apoptosis levels of SP101 in PLC26 cells were analyzed by Annexin V and PI staining. The PLC26 cells were trypsinized and then incubated with propidium iodide (5 µl) and Annexin V-FITC (5 µl) at room temperature for 5 mins before flow cytometry. Please refer to FIG. 22. The levels of Annexin V+/PI− cells (early apoptosis) and Annexin V+/PI+ cells (late apoptosis) were significantly increased by treatment with SP101 at 30 μM for 24 hours in PLC26 cells.

What is claimed is:

1. A method for overcoming EGFR-T790M mutation, comprising administering dodecyl 4-(4-(3-(4-(3-chloro-4-fluorophenylamino)-7-methoxyquinazolin-6-yloxy)propyl)piperazin-1-yl)-4-oxobutanoate (SP101) to a non-small cell lung carcinoma (NSCLC) cell, said SP101 having formula:

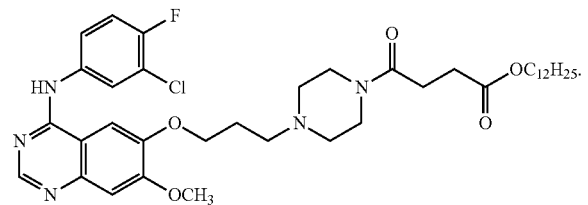

2. The method of claim 1, wherein the EGFR-T790M mutation comprises protein phosphorylation of EGFR and expression of Survivin protein.

3. The method of claim 1, wherein the SP101 reduces Survivin protein, induces activation of Caspase 3 protein and produces apoptosis.

4. The method of claim 1, wherein the EGFR-T790M mutation occurs in human non-small cell lung carcinoma.

5. A method for inhibiting cancerous stemness, comprising administering dodecyl 4-(4-(3-(4-(3-chloro-4-fluorophenylamino)-7-methoxyquinazolin-6-yloxy)propyl)piperazin-1-yl)-4-oxobutanoate (SP101) to a non-small cell lung carcinoma (NSCLC) cell, said SP101 having formula:

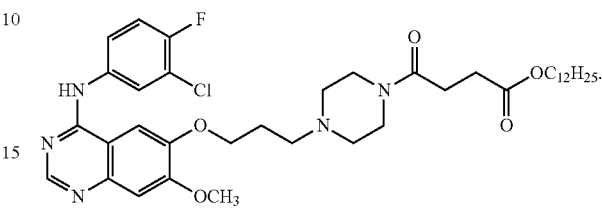

6. The method of claim 5, wherein the cancerous stemness comprises expressions of Oct4, Nanog and Survivin protein.

7. The method of claim 5, wherein the SP101 produces apoptosis.

8. The method of claim 5, wherein the cancerous stemness occurs in human non-small cell lung carcinoma.

* * * * *